United States Patent [19]

Griffon

[11] 4,292,312

[45] Sep. 29, 1981

[54] METHOD FOR PREPARING ALLOXAN STABLE AQUEOUS SOLUTIONS AND SOLUTIONS RESULTING THEREFROM

[76] Inventor: Henri Griffon, 72 Rue de Longchamps, 75782 Paris, France

[21] Appl. No.: 159,168

[22] Filed: Jun. 13, 1980

[30] Foreign Application Priority Data

Jun. 15, 1979 [FR] France ................................ 79 15363

[51] Int. Cl.³ ..................... A61K 31/00; A61K 47/00; A61K 31/505
[52] U.S. Cl. .................................. 424/176; 424/251; 544/298
[58] Field of Search ................. 424/176, 251; 544/298

[56] References Cited

U.S. PATENT DOCUMENTS 3,637,640 1/1972 Huber .............................. 424/176 X
3,728,454 4/1973 Douros et al. ...................... 424/251

OTHER PUBLICATIONS

Merck Index, 9th Ed., 1976, Entry No. 274.

*Primary Examiner*—Frank Cacciapaglia, Jr.
*Attorney, Agent, or Firm*—Darby & Darby

[57] ABSTRACT

Stable aqueous injectable solutions comprising alloxan stabilized with a reducing sugar selected from the group consisting of levulose, glucose and lactose are disclosed.

10 Claims, No Drawings

METHOD FOR PREPARING ALLOXAN STABLE AQUEOUS SOLUTIONS AND SOLUTIONS RESULTING THEREFROM

FIELD OF THE INVENTION

The present invention relates to a method for preparing a stable aqueous solution of alloxan.

BACKGROUND OF THE INVENTION

It is known that alloxan which is in powder form in its anhydrous, monohydrated or tetrahydrated state, is easily soluble in water. But alloxan and its solutions are very labile and deteriorate when subjected to air, light, or any temperature increase. Therefore, it is highly difficult to store and preserve them correctly.

OBJECT AND SUMMARY OF THE INVENTION

The object of the invention is to provide stable aqueous alloxan solutions, which can be handled and preserved without deterioration. This object of the invention is also useful as a technique for the progress of preparation and preservation of chemical products. Further, it has application in the preparation of alloxan solutions for therapeutic use.

It is known that alloxan is used with success in treating cancer according to the principles of Dr. Pierre Grobon, the creator of the cancer alloxan therapy.

The administration of alloxan is done exclusively by the intramuscular route, so that the medicament has to be in the form of injectable ampullae.

Hitherto, said ampullae were made by preparation of fractional doses of alloxan in solution, lyophilization and introduction of the powder thus obtained in an ampulla which was closed under nitrogen atmosphere so as to expel the air. At the moment of administration, an extemporaneous mixture of the powder and a few milliliters of physiological serum was made. This preparation method was particularly costly and did not give full satisfaction since the dry residue prepared under these conditions was often of pink coloration, demonstrating the existence of a deterioration of the alloxan.

The new method according to the invention provides for eliminating these disadvantages and provides the physician with an alloxan stable solution which is directly injectable and can be preserved.

The method of preparation according to the present invention is characterized in that an alloxan solution is prepared in water and in that there is added thereto, to the quantity by weight of pure alloxan present in the solution, a reducing sugar in a quantity by weight which is from 5 to 25 times larger than said alloxan quantity.

The reducing sugar can be glucose, lactose, and preferably levulose, which is notably the most soluble of the three sugars. One thereby benefits from the fact that the alloxan, being a reducing agent, very oxidizable even by the oxygen of the air, has its reducing potential increased if a reducing agent is added to the medium; and therefore the protection of the product is increased in proportion. Since the field of use is therapeutic, it has been found particularly advantageous to use reducing sugars as adjuvant reducing agents, and particularly those aforementioned, which are biological substances of obvious harmlessness.

The protecting action of the reducing sugar can be clearly demonstrated by effecting the following test:

When one adds ammonia to the mixed solution of alloxan and reducing sugar thus prepared, the latter remains colorless. This proves that the alloxan remains stable and is protected against any deterioration. In fact, the addition of ammonia to a simple alloxan solution brings about a pink coloration, which demonstrates the deterioration of alloxan by air and the ambient conditions.

In the particular case of the preparation of alloxan solution ampullae for therapeutic administration, the method according to the invention is the following:

One introduces in physiologic serum or in water for injectable solutions a predetermined quantity of alloxan, and one adds thereto a quantity 5 to 25 times larger of a reducing sugar. The sterilization of the solution can be carried out once it is introduced in 5 ml ampullae and once these ampullae are closed, through tyndallization sterilization at 60°–70° C.

The preferred embodiment of the invention also includes carrying out the sterilization of the solution, before introducing it in ampullae, by filtration on a filter membrane used in bacteriology, at room temperature.

The ampullae are filled and sealed under a sterile atmosphere and can be preserved at a maximum temperature of 40° C.

Direct sterilization in an autoclave at 120° C. brings about a yellowing of the solution contained in the ampulla, which indicates a deterioration at this high temperature in spite of the presence of the protecting sugar.

It is preferred that one chooses a quantity of reducing sugar which is equal to about 5 to 15 times the quantity of anhydrous alloxan introduced in the solution.

BRIEF DESCRIPTION OF EXAMPLES

The following examples are given for illustration of the present method of preparation of injectable ampullae, without limiting the invention.

EXAMPLE I

An alloxan solution is prepared by introducing for each milliliter of physiological serum:
- 10 mg of pure anhydrous alloxan, or 12.27 mg of monohydrated alloxan, or 15.07 mg of tetrahydrated alloxan,
- 150 mg of levulose.

When need be, the solution is filtrated, then subjected to a filtration on a filter membrane at room temperature. A 5 ml ampulla is filled with 4.5 to 4.6 ml of aqueous solution thus prepared, and is then sealed under sterile atmosphere.

Such an ampulla is adapted so that one can draw therefrom by means of an injection syringe mounted on a needle appropriate for intramuscular injections 4 ml of solution containing 40 mg of alloxan, which is the optimum unit dose for use with this product.

One can increase the quantity of levulose but a dose of 250 mg per milliliter should not be exceeded since there would be then the hazard of a phenomenon of carbonization of the sugar when closing the ampulla.

EXAMPLE II

An alloxan solution is prepared by introducing, for each milliliter of physiological serum:
- 10 mg of puralloxan,
- 200 mg of glucose.

This solution is filtered and introduced into sterile ampullae as in the previous example.

EXAMPLE III

An alloxan solution is made by introducing for each milliliter of physiological serum:
10 mg of pure alloxan,
250 mg of lactose.

This solution can be introduced in sterile ampullae if desired, as in the previous example.

EXAMPLE IV

An alloxan solution is prepared by introducing, for each milliliter of water for injectable solution:
10 mg of anhydrous pure alloxan, or 12.27 mg of monohydrated alloxan, or 15.07 mg of tetrahydrated alloxan,
50 mg of levulose (corresponding to an isotonic solution of levulose).

The solution obtained is filtered on a filter membrane at room temperature.

A 5 ampulla is filled and sealed under sterile atmosphere.

This ampulla contains 50 mg of alloxan and 250 mg of levulose. The ampullae are stored at 4° C. maximum and preferably in darkness.

The prevention of deterioration of the alloxan has been studied by spectrophotometry in ultraviolet light.

It is known that in an alcoholic medium, the alloxan displays an absorption spectrum in ultraviolet light characterized by a maximum at 272 millimicrons and a minimum at 262 millimicrons.

Comparative measurements have been made on alloxan solutions prepared according to the method of the invention (with a reducing sugar and particularly levulose) and on solutions containing the same quantity of alloxan but as a physiological serum without levulose.

The spectal curves of the alloxan in these two types of solution have been plotted against time.

It was thus established that only the solutions where the alloxan was associated with levulose displayed a remarkable stability for at least 1 year.

What is claimed is:

1. A method for preparing a stable, aqueous solution of alloxan, which comprising:
    dissolving in an aqueous fluid a predetermined quantity by weight of alloxan and adding from about 5 to 25 times the weight of said alloxan of at least one sugar selected from the group consisting of levulose, glucose and lactose to said fluid.

2. The method according to claim 1, wherein the sugar is levulose.

3. The method according to claim 1, wherein the sugar is glucose.

4. The method according to claim 1, wherein the sugar is lactose.

5. A method for preparing a stable, injectable aqueous alloxan solution which comprises:
    dissolving in physiological serum a predetermined quantity by weight of alloxan, adding from about 5 to about 25 times the weight of said alloxan of at least one sugar selected from the group consisting of levulose, glucose and lactose to said serum, filtering the serum, introducing said serum into a 5 ml ampule, sealing the ampule with a burner and sterilizing the ampule through tyndallization between about 60° C. to about 70° C.

6. A method for preparing stable, injectable aqueous alloxan solutions introduced in sterile ampullae, which comprises:
    dissolving in water a predetermined quantity by weight of alloxan, adding from about 5 to about 25 times by weight of said alloxan of at least one sugar selected from the group consisting of levulose, glucose and lactose to said water, filtering said water with a bacteriological membrane, introducing the water under a sterile atmosphere into an ampule and sealing said ampule with heat.

7. The method according to claim 6, which further comprises adding about 10 mg of pure anhydrous alloxan and about 50 mg of levulose for each 1 ml of water in said solutions.

8. A method for preparing a stable aqueous solution containing a predetermined quantity by weight of alloxan, which comprises:
    adding from about 5 to about 25 times the weight of said alloxan of at least one sugar selected from the group consisting of levulose, glucose and lactose to said solution.

9. A pharmaceutical formulation comprising:
    a solution containing a predetermined quantity by weight of alloxan dissolved in water or physiological serum, said solution containing from about 5 to about 25 times the weight of said alloxan of a reducing sugar selected from the group consisting of levulose, glucose and lactose.

10. The pharmaceutical formulation according to claim 9, further comprising for each ml of water, about 10 mg of alloxan and about 50 mg of levulose.

* * * * *